(12) United States Patent
Easton (10) Patent No.: US 7,544,007 B2
(45) Date of Patent: Jun. 9, 2009

(54) SWIVEL ADAPTER AND BASE UNIT HANDLE

(75) Inventor: Kevin R. Easton, Cincinnati, OH (US)

(73) Assignee: Integra LifeSciences Corporation, Plainsboro, NJ (US)

(*) Notice: Subject to any disclaimer, the term of this patent is extended or adjusted under 35 U.S.C. 154(b) by 366 days.

(21) Appl. No.: 10/549,876

(22) PCT Filed: Mar. 10, 2004

(86) PCT No.: PCT/US2004/007327

§ 371 (c)(1),
(2), (4) Date: Sep. 16, 2005

(87) PCT Pub. No.: WO2004/084751

PCT Pub. Date: Oct. 7, 2004

(65) Prior Publication Data

US 2006/0190010 A1  Aug. 24, 2006

(51) Int. Cl.
*A61F 5/00* (2006.01)
(52) U.S. Cl. .............. 403/322.4; 602/17; 128/845; 128/869; 5/622; 5/637
(58) Field of Classification Search ............ 403/322.1, 403/322.4; 602/17; 128/845, 869; 606/1, 606/130; 5/622, 637, 622.637; 81/363, 368
See application file for complete search history.

(56) References Cited

U.S. PATENT DOCUMENTS

| 2,320,303 | A | * | 5/1943 | Ross ......................... 81/363 |
| 3,340,754 | A | * | 9/1967 | Burchett ..................... 81/356 |
| 3,572,835 | A | | 3/1971 | Kees, Jr. et al. |
| 4,964,748 | A | | 10/1990 | McFadden |
| 5,177,823 | A | * | 1/1993 | Riach ......................... 5/622 |
| 5,276,927 | A | | 1/1994 | Day |
| 5,528,965 | A | * | 6/1996 | Finn .......................... 81/363 |
| 5,560,728 | A | | 10/1996 | McFadden |
| 5,564,663 | A | | 10/1996 | Cook et al. |
| 5,891,157 | A | | 4/1999 | Day et al. |
| 2002/0133174 | A1 | | 9/2002 | Charles et al. |

* cited by examiner

*Primary Examiner*—Michael P Ferguson
(74) *Attorney, Agent, or Firm*—Wood, Herron & Evans, L.L.P.

(57) ABSTRACT

A swivel adapter (26) has a base (60) with an outward facing first side (57) and a pivot surface (55) extending from the first side. A Center adapter (52) is mounted for pivoting motion on the pivot surface and has an outward facing first device connector (46). A clamp (78) has a clamp operator (80) operable to clamp the center adapter on the pivot surface at a desired orientation with respect to the base. A base unit handle (34) has a clamping mechanism (128, 138, 156, 164) connected to a body (120) having two split bores (36, 122), which is operable to clamp and unclamp the split bores on respective shafts. The clamping mechanism has linkage (138, 156) connected to a closing handle (164) to provide a mechanical advantage to the handle during the clamping action.

7 Claims, 6 Drawing Sheets

SWIVEL ADAPTER AND BASE UNIT HANDLE

FIELD OF THE INVENTION

This invention relates generally to neurosurgical apparatus and more particularly, to an improved apparatus for supporting a head of a patient.

BACKGROUND OF THE INVENTION

During neurological or other procedures to the head and neck areas of a patient, it is common for the patient to lie on a table with the patient's head at or extending beyond the end of the table. A head support, designed to hold the patient's head during a surgical procedure, is mounted on a swivel adapter that, in turn, is mounted on a mechanical connector or "base unit." The base unit is attached at the end of the table. The base unit has movable elements that permit the head support and swivel adapter to be adjusted and clamped at a position and orientation having a desired elevation and longitudinal position with respect to the table. The head support may be a skull clamp which securely and rigidly holds a patient's head in the desired position and orientation. Alternatively, the patient's head may be supported by a head rest, for example, a horseshoe-shaped headrest, or general purpose headrest.

Typically, the head support is coupled to one end of the swivel adapter which is an angled connector preferably providing two degrees of rotational freedom. The other end of the swivel adapter is connected to an upper end of a swivel arm or transitional arm of the base unit. The transitional arm is used to change the elevation of the head support. A shaft on the other end of the transitional arm is located within a bore of one end of the base unit handle. The other end of the base unit handle is rotationally coupled to a generally U-shaped frame which may be longitudinally and/or laterally adjusted with respect to the end of the table. Therefore, by rotationally adjusting the transitional arm with respect to the frame, and further adjusting the position of the frame relative to the table, the head support can be moved into any desired position and orientation.

The transitional arm and base unit handle are locked in desired positions and orientations by operating a closing handle on the base unit handle. One end of a cam rod in the base unit handle is pulled to apply locking forces at both ends of the base unit handle. The locking forces slightly collapse relieved openings that intersect holes at opposite ends of the base unit handle, thereby locking the base unit handle to the shaft on one end of the transitional arm and the U-shaped frame.

While such a construction has proven satisfactory, recent surgical procedures require that more devices be mounted in the area of the head support and swivel adapter, for example, reference arms of a navigation system. To facilitate such devices, it is known to connect an auxiliary arm to a starburst connector on an outer side of the skull clamp. The auxiliary arm has starburst connectors at opposite ends of the arm to which additional devices may be attached. With the auxiliary arm mounted on the outer side of the skull clamp facing outward from the swivel adapter, it is then necessary that the swivel adapter be mounted to a starburst connector on an inner side of the skull clamp facing inward toward a patient and the operating table. Such an arrangement requires that a user reach around the skull clamp and the patient's head in order to adjust and manipulate the swivel adapter. Such an arrangement is awkward in use; and therefore, there is a need to provide a capability of mounting additional devices while maintaining the swivel adapter on the side of the skull clamp facing outward from the swivel adapter and generally toward the user. With such an arrangement, all of the devices can be easily and quickly manipulated by the user.

When additional devices are mounted in the area of the head support and swivel adapter, an additional load is imposed on the base unit handle. Thus, the clamping forces applied by the base unit handle must be correspondingly greater in order to hold the skull clamp and swivel adapter stable during the surgical procedure. With known base unit handles, the closing handle directly creates the locking forces; and a substantial force must be manually applied to the closing handle in order to provide the necessarily greater clamping forces to support the additional devices. While some persons may have the physical strength to apply such larger forces to the closing handle, others may not; and consequently, the base unit handle may slip or move slightly during use. Therefore, there is a need to provide a base unit handle that can be operated to provide the clamping forces necessary to support additional devices on the swivel adapter without requiring a proportionally greater force to operate the closing handle.

SUMMARY OF THE INVENTION

The present invention provides a multi-starburst swivel adapter that has additional starburst connectors that face outward from the swivel adapter. The multi-starburst swivel adapter of the present invention is attachable to a side of a head support that also faces outward from the swivel adapter and generally toward the user and therefore, is easily adjusted and manipulated by the user. The present invention further provides a base unit handle with linkage generating a mechanical advantage to the force being applied to the closing handle; and therefore, greater clamping forces can be more easily generated by a user. The multi-starburst swivel adapter and base unit handle of the present invention are especially useful when it is desired to mount additional devices near a head support.

According to the principles of the present invention and in accordance with the described embodiments, the invention provides a swivel adapter having a base with an outward facing first side and a pivot surface extending from the first side. A center adapter is mounted for pivoting motion on the pivot surface and has an outward facing first device connector. A clamp has a clamp operator operable to clamp the center adapter on the pivot surface at a desired orientation with respect to the base, and unclamp the center adapter from the pivot surface. Thus, the swivel adapter permits the device connector to be used and the center adapter to be manipulated and adjusted from a common side of the swivel adapter.

In one aspect of the invention, the center adapter has a split bore; and the clamp operator has a handle pivotally connected to the center adapter on one side of the split bore. A rocker has one end pivotally connected to the center adapter on an opposite side of the split bore, and the rocker has a first shoulder at an opposite end. A rod has one end pivotally connected to the handle and a second shoulder at an opposite end, and a biasing means is disposed between the first shoulder and the second shoulder. The handle is movable between unclamp and clamp positions to respectively release and secure the center adapter with respect to the base.

In another aspect of the invention, a threaded member extends in an outward facing direction beyond the pivot surface; and a knob is disposed against an outward facing side of the center adapter and engageable with the threaded member.

Tightening the knob on the threaded member locks the center adapter against the base at a desired orientation, and loosening the knob releases the center adapter to be pivotable on the pivot surface. All of the swivel adapter components in this embodiment are made of radiolucent materials.

In a further embodiment of the invention, a base unit handle is connectable to a shaft of a transitional arm and a bar of a frame. The base unit handle has a body with first and second split bores adapted to receive the shaft and the bar, respectively. A clamping mechanism is connected to the body and is operable to clamp and unclamp the first and second split bores on the respective shaft and bar. The clamping mechanism has a rod with one end connected to the body. A closing handle and linkage are connected between an opposite end of the rod and one end of the closing handle. The linkage provides a mechanical advantage in transferring a force being applied on the closing handle to the rod. Thus, a user of the base unit handle is able to more easily close the base unit handle to support larger loads.

These and other objects and advantages of the present invention will become more readily apparent during the following detailed description taken in conjunction with the drawings herein.

DETAILED DESCRIPTION OF THE INVENTION

Figure 1:
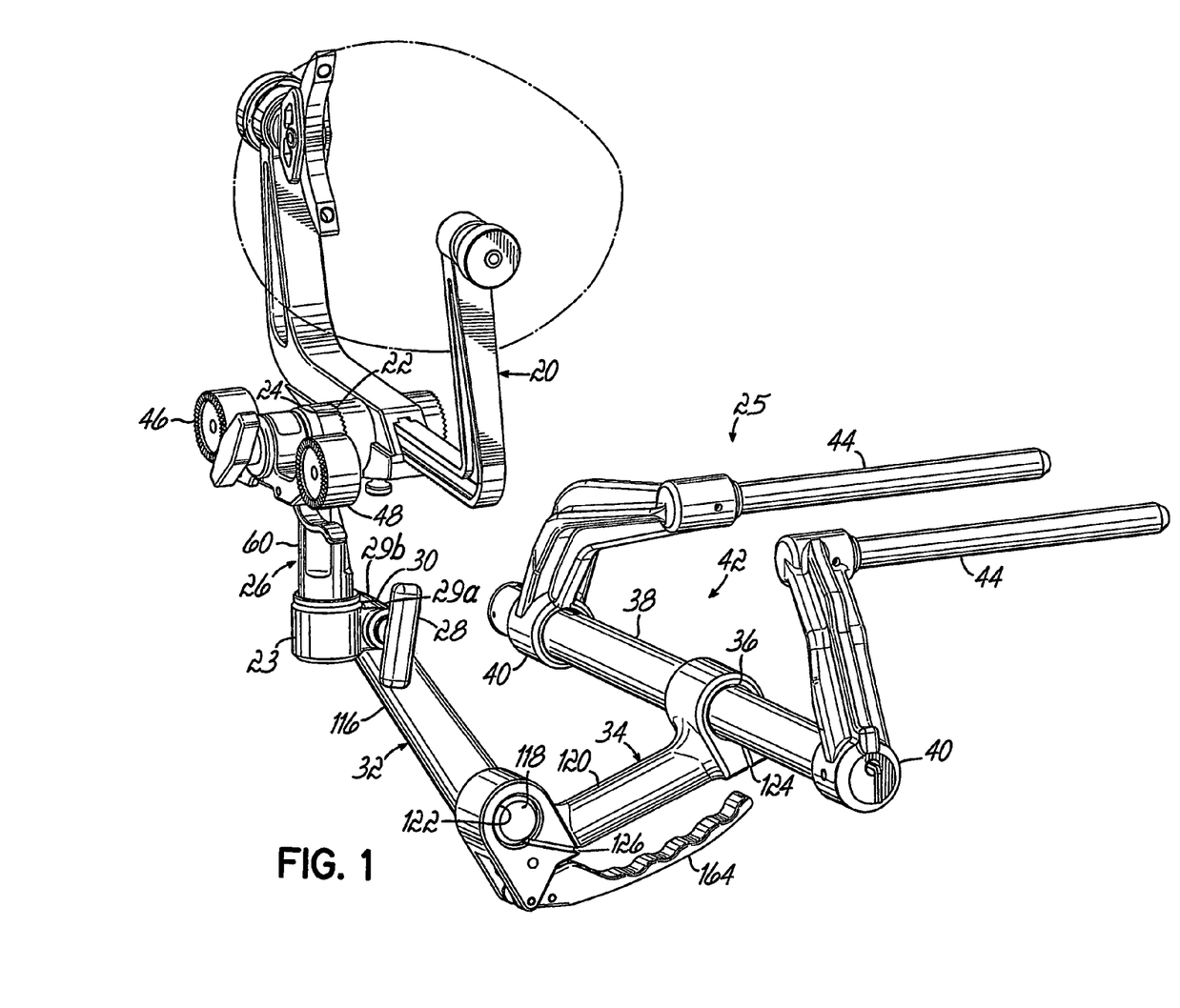
FIG. 1 is a perspective view of a multi-starburst swivel adapter and base unit in accordance with the principles of the present invention.

Referring to FIG. 1, a patient's head is supported by a head support 20, for example, a skull clamp. The skull clamp 20 is supported by a multi-starburst swivel adapter 26, that, in turn, is supported by a base unit 25. The base unit 25 is comprised of a transitional arm 32, base unit handle 34 and U-shaped frame 42. The skull clamp 20 has a toothed or starburst connector 22 that is connectable to a mating starburst connector 24 on a multi-starburst swivel adapter 26. The multi-starburst swivel adapter 26 has a pair of device connectors 46, 48, for example, starburst connectors, that have respective receiving surfaces facing or directed outward from the swivel adapter and generally toward the user. For purposes of this document, "outward from the head support", "outward from the swivel adapter" and "outward from the swivel adapter base" means in an outward direction generally extending away from the head support 20, that is, facing the left edge of FIG. 2. It is understood that a user may be positioned at the end of the base unit, that is, at the left side of FIG. 2, or to one side or the other of the head support 20 while operating the swivel adapter 26. The starburst connectors 46, 48 are used to mount additional devices, for example, reference arms of a navigation system. A swivel sleeve 23 is rotatably mounted on a lower end of the swivel adapter 26, and torque screw 28 extends through locking tabs 29a, 29b of a split bore in the swivel sleeve 23 and is threaded into an upper end of the transitional arm 32. An outer directed surface of locking tab 29b and the upper end of the transitional arm 32 have opposing interlockable starbursts 30. The base unit handle 34 has an outer bore 36 for receiving a crossbar 38 supported at its ends by end brackets 40. The crossbar 38 and end brackets 40 form the generally U-shaped frame 42 that is mounted to an operating table (not shown) by support shafts 44 in a known manner.

Figure 2:
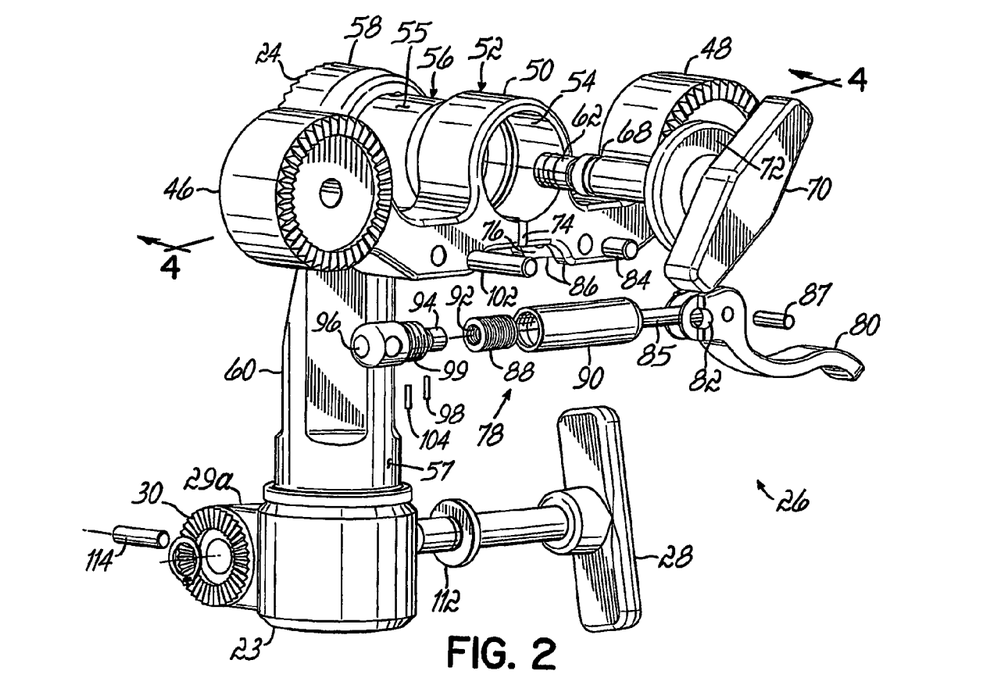
FIG. 2 is disassembled perspective view of one embodiment of the multi-starburst swivel adapter of FIG. 1.
Figure 3:
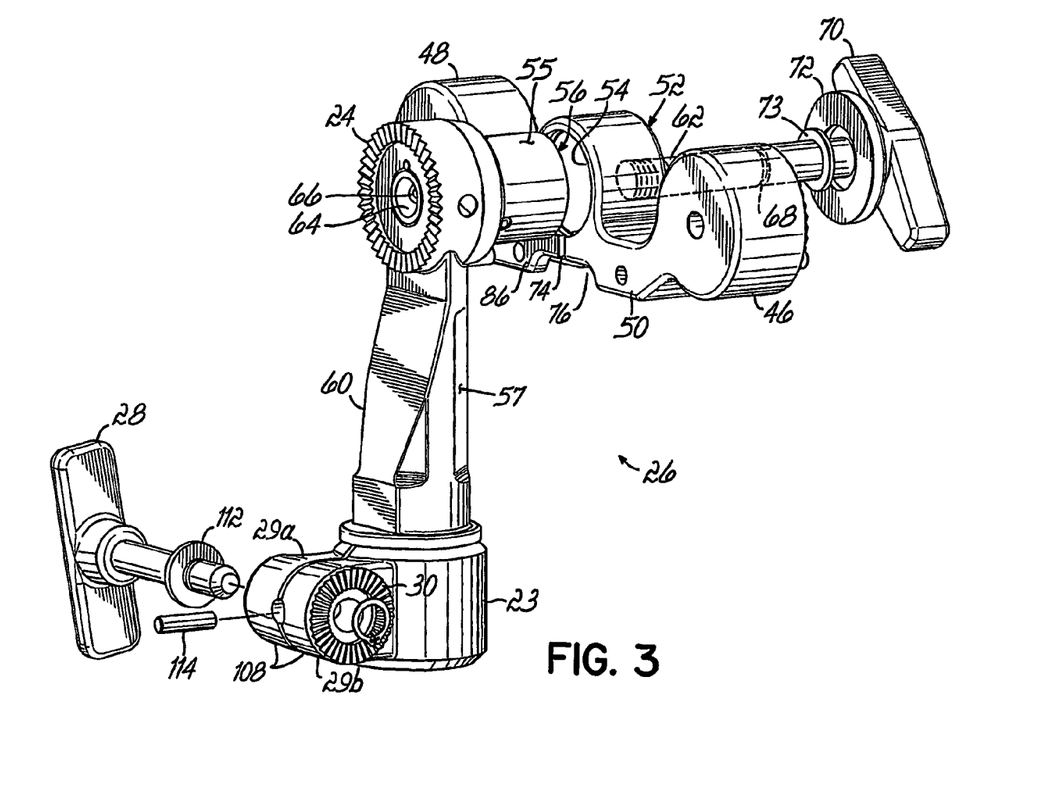
FIG. 3 is another disassembled perspective view of the multi-starburst swivel adapter of FIG. 1.

Referring to FIGS. 2 and 3, the auxiliary starburst connectors 46, 48 are disposed on opposite ends of a body 50 of a center adapter 52. The center adapter 52 has a bore 54 that pivotally receives a pivot or bearing surface 55 on a cylindrical boss 56 that is threaded and pinned into an outward facing first side 57 at an upper end 58 of a swivel adapter base 60. The cylindrical boss 56 functions as a pivot pin or surface for the center adapter 52. A screw 62 is insertable through a bore 64 shown in FIG. 3. The bore 64 extends through the boss 56, the base upper end 54, starburst 24; and thus, the screw 62 is engagable in a threaded centerhole of the starburst connector 22 of FIG. 1. As shown in FIG. 3, opposed, spring-biased ball detents 66 are mounted in the bore 64 and are disposable in the annular slot 68 (FIG. 2) in the screw 62. The ball detents 66 and slot 68 allow the screw 62 to be easily removed for cleaning. The screw 62 also has a handle 70 on its distal end and a retainer 72 that limits axial travel of the center adapter 52 when is not locked onto the boss 56. When the handle 70 is used to tighten the screw 62 into the starburst 22 of FIG. 1, referring to FIG. 3, a nylon washer 73 provides a bearing surface for applying a tightening force against the boss 56.

A lower portion of the center adapter body 50 has a slot 74 extending thereacross, which intersects and forms a split in the bore 54. Thus, the slot 74 permits the split bore 54 to be collapsed and clamp around the boss 56 to secure the center adapter 52 at a desired angular orientation. A lower side of the center adapter 52 has a slotted opening 76 for receiving a center adapter clamp 78 that is effective to expand and collapse the split bore 54.

Referring to FIGS. 2-5, the center adapter clamp 78 has a clamp operator or closing handle 80 that has holes 82 on one end for receiving opposed pivot pins 84 mounted in opposite walls 86 of the center adapter body 50. The one end of the closing handle 80 is also pivotally connected to one end of a cam transfer rod 85 by a dowel pin 87. A plurality of Bellville spring washers 88 are located in a center bore of a tubular spring adjuster 90. In some applications, there may be more than twenty Bellville spring washers. The spring adjuster 90 has an internal shoulder 91 (FIG. 4) that prevents spring washers 88 from passing through the spring adjuster 90. The cam transfer rod 85 passes through center holes 92 in the spring washers 90 and has an opposite end threaded into a piston cap 94. The piston rod 94 forms a shoulder 95 on the opposite end of the cam transfer rod 85 for retaining the Bellville spring washers 88. A roll pin 98 is used to secure the piston cap 94 to the cam transfer rod 85. The spring adjuster 90 is threaded onto a surface 99; and one end of the piston cap 94 retains the spring washers 90 between the piston cap 94 and the spring adjuster 90. The rocker 96 is pivotally mounted on opposed pins 102 extending through the opposite walls 86 of the center adapter body 50. Thus, the rocker 96 and cam transfer rod 85 are able to pivot with respect to coincident centerlines of the pins 102. After closing handle 80 is assembled onto the center adapter 52, the spring adjuster 90 is rotated to achieve a desired spring tension with the spring washers 88; and thereafter, the spring adjuster 90 is secured in that position by a roll pin 104.

A swivel sleeve 23 is rotatably mounted on a lower end of the swivel adapter base 60. The swivel sleeve 23 has a split bore that is used to secure the swivel adapter body 60 at a desired orientation by tightening an releasing opposed locking tabs 29a, 29b. A torque screw 28 extends through the locking tabs 29a, 29b and is threaded into a mating starburst connector, not shown. A bearing washer 112 applies the locking force. A retaining pin 114 extends through a sidewall of the swivel sleeve 23, and into an annular slot in a lower end of the swivel adapter body 60. Thus, the swivel sleeve 23 is able to freely rotate with respect to the body 60; but the swivel sleeve 23 cannot be removed from the body 60.

Figure 4:
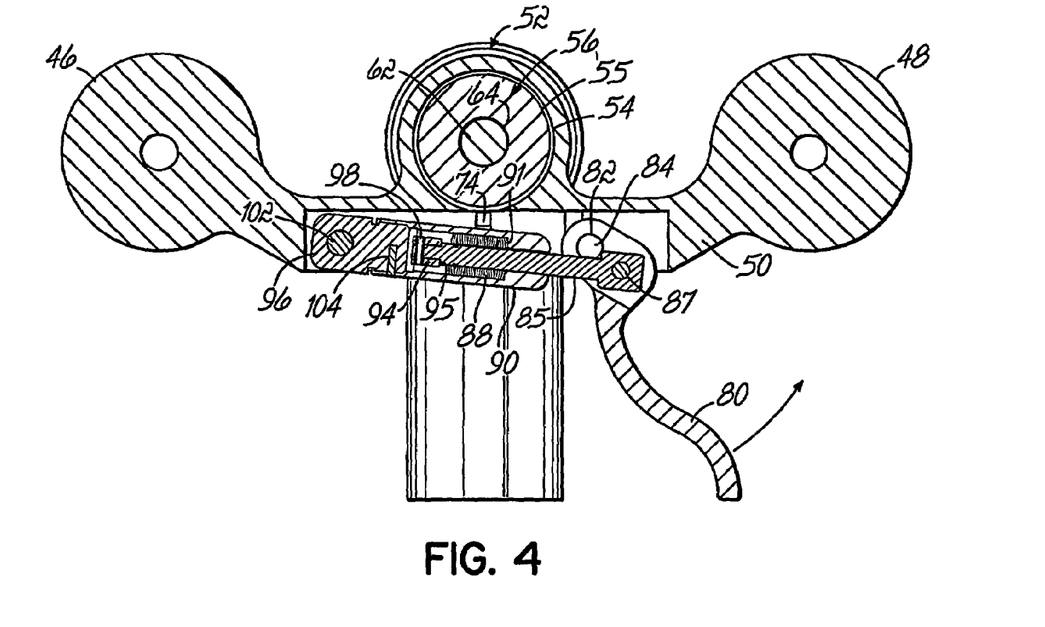
FIG. 4 is partial cross-sectional view illustrating an unclamped state of the multi-starburst swivel adapter of FIG. 2.
Figure 5:
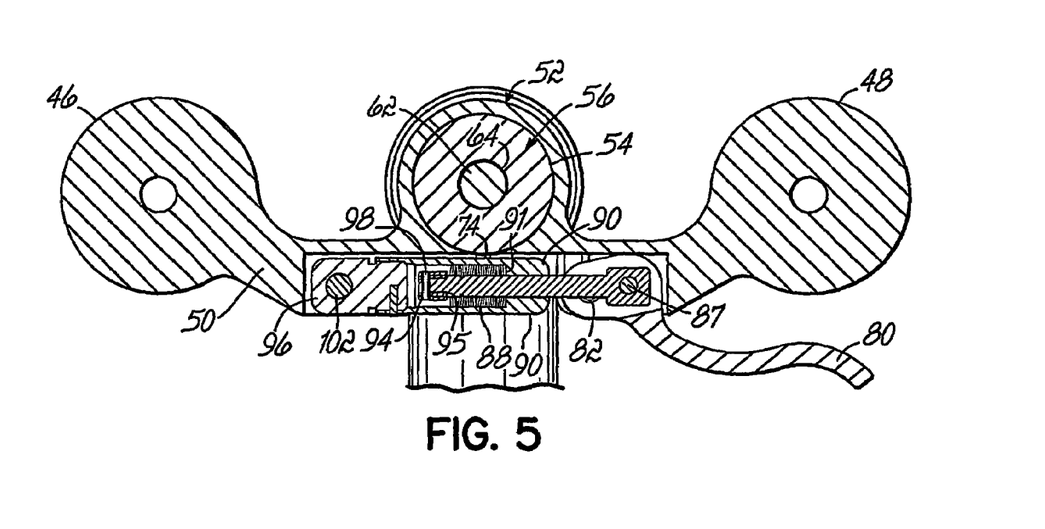
FIG. 5 is partial cross-sectional view illustrating a clamped state of the multi-starburst swivel adapter of FIG. 1.

With the closing handle 80 in the open position illustrated in FIG. 4, the gap 74 is wide and the center adapter body 50 is freely rotatable about the boss 56. To lock the center adapter 52, the closing handle 80 is pivoted counterclockwise as viewed in FIG. 4 and pushed toward the starburst connector 48 to a closed position illustrated in FIG. 5. During that motion, the closing handle 80 pivots with respect to coincident centerlines of the pins 84; and that pivoting motion moves the cam transfer rod 85 slightly from left to right as viewed in FIG. 4 to the position illustrated in FIG. 5. Further, that motion by the transfer rod 85 is effective to slightly collapse the gap 74 and reduce the size of the split bore 54, thereby applying a clamping force around the boss 56 and securing the center adapter 52 at a desired angular orientation with respect to the center boss 56. The operation of moving the handle 80 to the closed position of FIG. 5 also compresses the Belleville spring washers 88 between the adjuster 90 and the piston cap 94, which provides a spring biased force to facilitate moving the handle 80 back to its open position of FIG. 4. Thus, the multi-starburst swivel adapter 26 of FIG. 2 includes additional starburst connectors 46, 48 that face outward from the base 60. Therefore, additional devices can be easily and quickly mounted with respect to the head support 20. Further, the closing handle 80 also positioned on an outward side of the base 60, so the that multi-starburst swivel adapter can be easily mounted and used.

Referring back to FIG. 1, the additional starburst connectors 46, 48 of the multi-starburst swivel adapter 26 are used to support additional components. The weight of such components puts a greater load on an upper end 116 of the transitional arm 32. That additional load as leveraged by the length of the transitional arm 32 must also be supported by the base unit handle 34. Therefore, the clamping forces applied by the base unit handle 34 to a lower end shaft 118 of the transitional arm 32 and the crossbar 38 must be correspondingly greater. The base unit handle 34 is capable of providing an adjustable clamping force, so that a greater clamping force is applied on the shaft 118 of the transitional arm 32 and the cross bar 38 in the event of heavier loads. However, with known base unit handles, greater clamping forces require that the closing handle be manually operated with a proportionally greater force; and that can prove problematic in an environment where some users may not have the physical strength to apply such a greater force.

Figure 6:
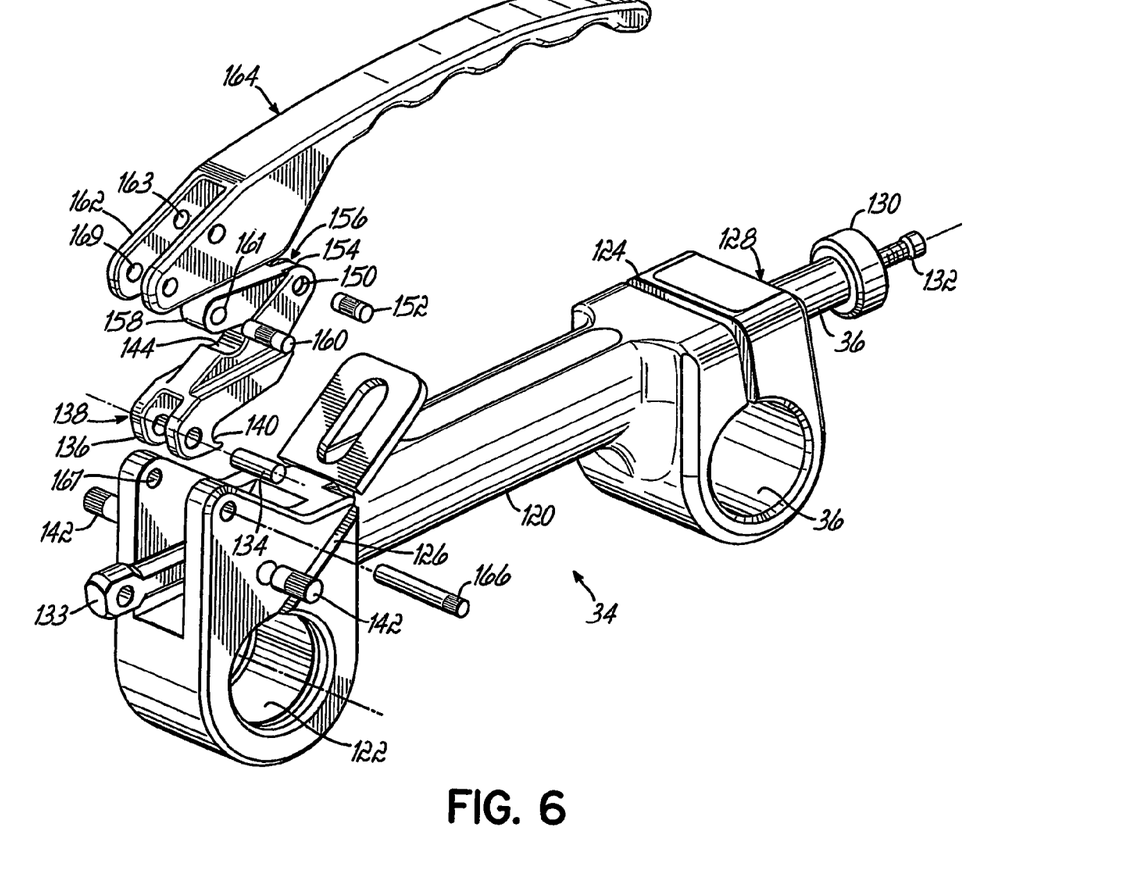
FIG. 6 is disassembled perspective view the base unit handle of FIG. 1.

Referring to FIGS. 1 and 6, an improved base unit handle 34 has a body 120 with a split outer bore 36 that receives the crossbar 38. An inner bore 122 receives a shaft 118 extending from the transitional arm 32. The body 120 has an outer slot 124 extending thereacross, which intersects and forms a split in the outer bore 36. The outer slot 124 permits the outer bore 36 to be slightly increased and decreased in size to provide a clamping action on the crossbar 38. The base unit handle body 120 further has an inner slot 126 extending thereacross, which intersects and forms a split in the bore 122. Thus, the inner slot 126 permits the inner bore 122 to be slightly increased or decreased in size to provide a clamping force against the shaft 118. A cam rod 128 extends longitudinally through the base unit handle body 120 and has an adjusting nut 130 threadedly connected to an outer end 131 of the cam rod 128. The cam rod outer end 131 is split and has a threaded center bore 135. As a tapered locking screw 132 is tighten into the centerbore, the cam rod outer end 131 is spread apart, thereby locking the adjusting nut 130 onto the cam rod 128.

The inner end 133 of the cam rod 128 is pivotally connected by a pin 134 to a pair of inner ears 136 of a cam link 138. The pair inner ears 136 have respective hooks 140 that contact a pair of opposed bearing pins 142 extending laterally through the base unit handle body 120. The pins 142 have a length providing a bearing pivot surface for the cam link 138 but are separated by a distance permitting the cam rod 128 to pass therebetween. An outer end 150 of the cam link 138 is pivotally connected by a pin 152 to an outer end 154 of a transfer link 156. An inner end 158 of the transfer link 156 is pivotally connected to an inner end 162 of a closing handle 164 by a pivot pin 160 extending through holes 161 and 163. Pin 166 extends through holes 167 of the body 120 and holes 169 closing handle 174. The cam link 138 further has a clearance opening or detent 144 that receives the pin 166, which provides a stop for the closing handle 164 as it is moved to its open position as shown in FIG. 7.

Figure 7:
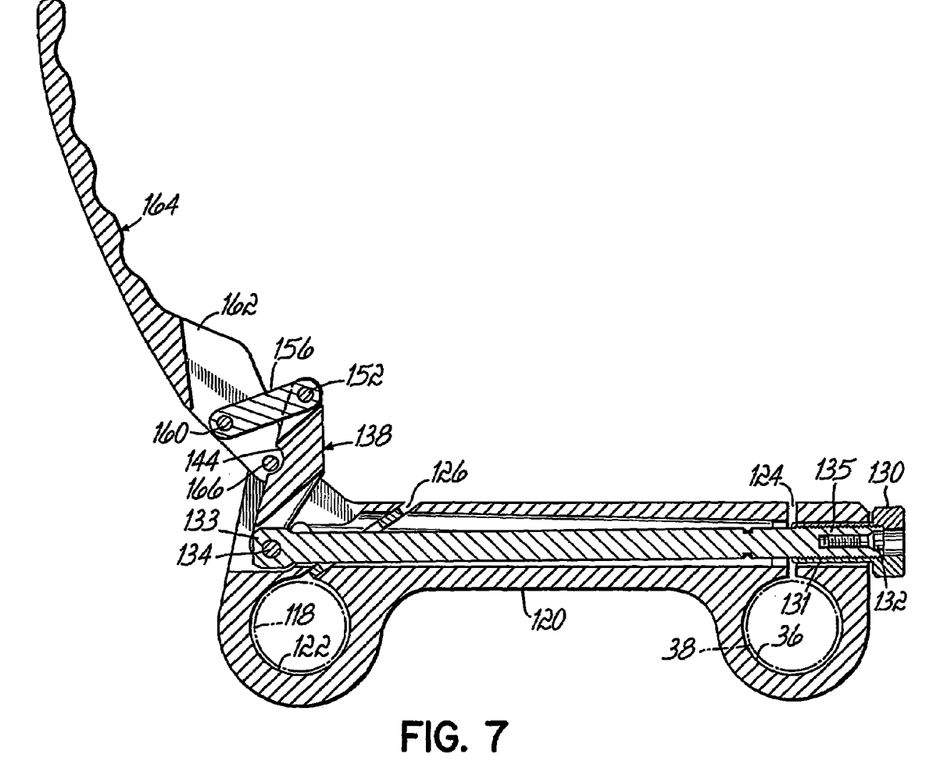
FIG. 7 is partial cross-sectional view illustrating an unclamped state of the base unit handle of FIG. 6.
Figure 8:
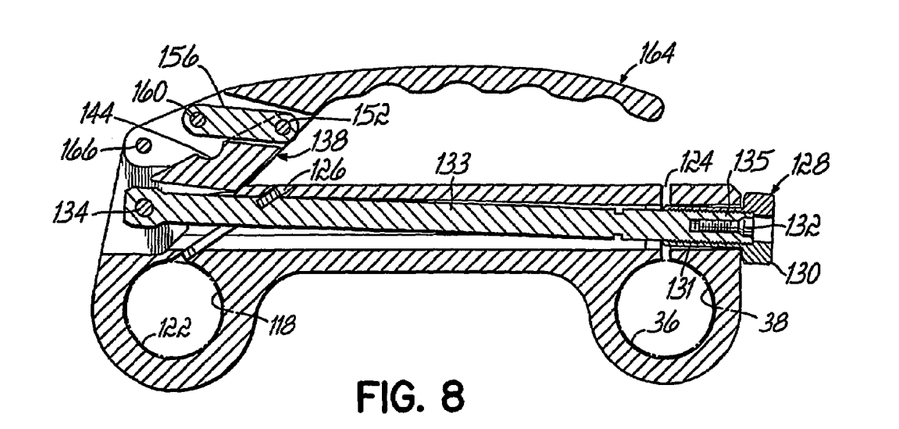
FIG. 8 is partial cross-sectional view illustrating a clamped state of the base unit handle of FIG. 6.

With the closing handle 164 in the open or unclamped position illustrated in FIG. 7, the gaps 124, 126 are relaxed and at their most open state. Therefore, the crossbar 38 is freely movable within the outer bore 36; and the shaft 118 is also freely movable within the inner bore 122. When the base unit handle is properly positioned, the user moves the closing handle 164 from left to right as viewed in FIG. 7 to a closed or clamped position where the closing handle 164 is located against an upper side of the base unit handle body 120 as shown in FIG. 8. Motion of the closing handle 164 from right to left results in the cam rod 128 being placed in tension. Those tension forces cause the gaps 124, 126 to collapse slightly, thereby slightly reducing the size of the respective split bores 36, 122 and tightly clamping the shafts 38, 118 within the respective split bores 36, 122 of the base unit handle 34.

The arrangement of the closing handle 164 with the transfer link 156 and the cam link 138 provides the user with a mechanical advantage in creating a tension force in the cam rod 128. For example, for a given force applied to the closing handle 164, a tension force will be imposed on the cam rod 128 that is approximately 1.5-2 times greater than the tension force imposed on cam rods with known base unit handles. Thus, with the improved base unit handle 34, substantially greater clamping forces can be applied on the crossbar 38 and transitional arm shaft 118 in response to any given force applied to the closing handle 164 when compared to known base unit handles. With the mechanical advantage of the base unit handle of the present invention, a wide range of users can apply greater clamping forces that may be required by the mounting of additional devices to the multi-starburst connectors 46, 48 of FIG. 1.

Figure 9:
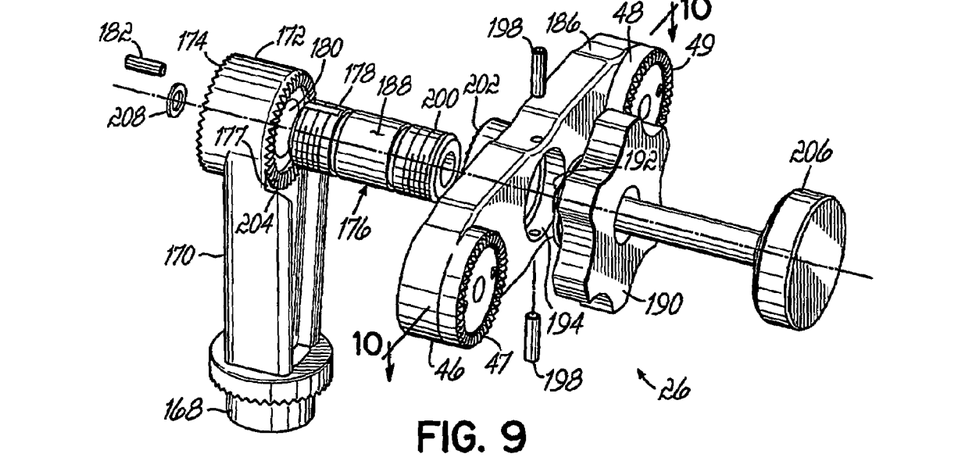
FIG. 9 is a disassembled perspective view of another embodiment of the multi-starburst swivel adapter of FIG. 1.
Figure 10:
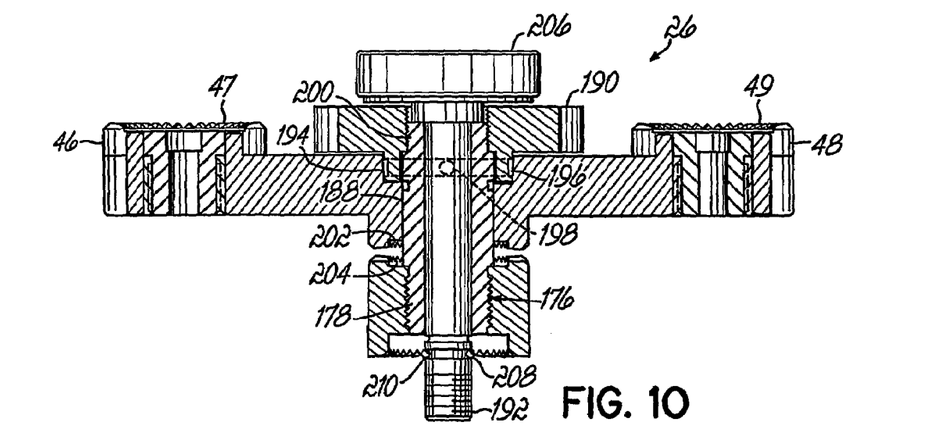
FIG. 10 is partial cross-sectional view illustrating an unclamped state of the multi-starburst swivel adapter of FIG. 9.
Figure 11:
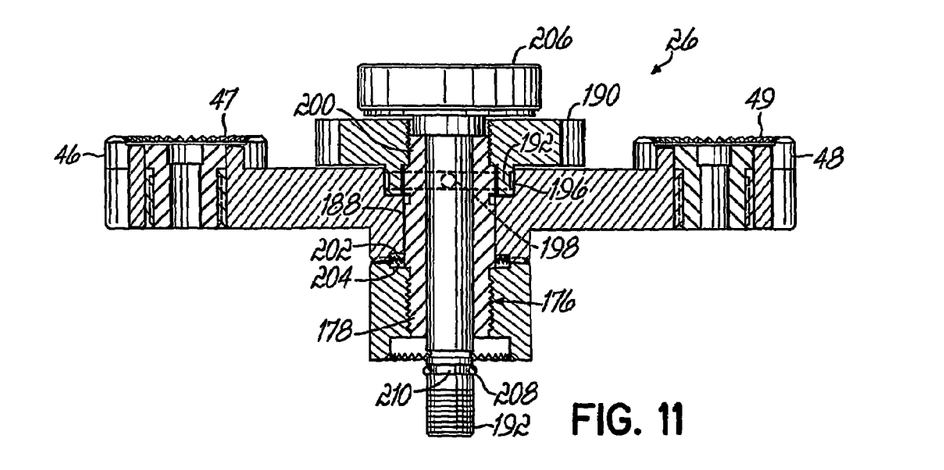
FIG. 11 is partial cross-sectional view illustrating a clamped state of the multi-starburst swivel adapter of FIG. 9.

The multi-starburst swivel adapter 26 illustrated with respect to FIGS. 2-5, is manufactured from metal components, which are incompatible with certain scanning procedures, for example, MRI scans. To accommodate procedures which require a base unit having radiolucent components, an alternative embodiment of the multi-starburst swivel adapter 26 is illustrated in FIGS. 9-11. All of the components comprising the multi-starburst swivel adapter 26 of FIG. 2 are made from radiolucent materials, for example, radiolucent polyethersulfone (PES), other carbon composite materials, phenolic, sapphire, wood, other radiolucent materials commercially available under the names of "DELRIN", "PEEK", "ULTEM", or other materials that produce a minimum of artifacts during an MRI scanning process. A swivel adapter 170 has a shaft 168 mountable to an upper end 116 (FIG. 1) of a transitional arm 32 utilizing a swivel sleeve 23 as previously described with respect to FIG. 2. An upper end 172 of the swivel adapter 170 has a first starburst 174 that is connectable to a mating starburst 22 (FIG. 1) of a head support 20. A centerpost 176 has a threaded inner end 178 that is threaded into a bore 180 on outward facing first side 177 of the swivel adapter 170. After the centerpost 176 is fully threaded into the bore 180, a hole is drilled through the mated threads on the inner end 178 and the bore 180. A locking pin 182 is then inserted in the hole to lock the centerpost 176 against rotation within the bore 180.

A center adapter 186 is slidable over the centerpost 176 and has an internal center bore that mounts over a cylindrical boss providing pivot or bearing surface 188 on the centerpost 176. Thus, the center adapter 186 is able to rotate with respect to the centerpost 176. An internal locking knob 190 has a shaft 192 (FIG. 10) extending into a bore 194 of the center adapter. The shaft 192 has an annular slot 196 that is sized to receive opposed pins 198 (FIG. 9) that extend through the center adapter and into the slot 196. Thus, the internal locking knob 190 is able to rotate freely with respect to the center adapter 186 but cannot be separated therefrom. The internal locking knob 190 has a threaded center bore extending through the shaft 192, which permits the internal locking knob 190 allows the starburst connector 202 to separate from starburst connector 204 as shown in FIG. 10. With the internal locking knob 190 loosened, the center adaptor 186 is able to pivot on center post 176 to a desired orientation. When that orientation is achieved, the internal locking knob 190 is tightened and starburst connector 202 is brought into engagement with starburst connector 204 as shown in FIG. 11, thereby locking the center adaptor 186 in its desired orientation.

A clamp operator or pass-through screw 206 passes through the centerpost 176 and the starburst 174 and is engagable with a threaded center hole in the starburst 22 (FIG. 1) of head support 20. An O-ring 208 is located in an annular slot 210 (FIG. 10) and prevents the pass-through screw 206 from sliding back through the centerpost 176. Thus, the multi-starburst swivel adapter 26 of FIG. 9 is fully radiolucent and includes starburst connectors 46, 48 that face outward from the swivel adapter 170. Therefore, additional devices can be easily and quickly mounted with respect to the head support 20. Further, the internal locking knob 190 and screw 206 also face outward from the swivel adapter 170, so the that multi-starburst swivel adapter 26 can be easily mounted to the head support and adjusted.

The multi-starburst swivel adapter 26 provides outward facing starburst connectors to which can support additional devices, for example, reference arms of a navigation system. The multi-starburst swivel adapter 26 is attachable to an outward facing side of a head support and therefore, is easily mounted, adjusted and manipulated by the user. The base unit handle 34 has additional linkage that generates a mechanical advantage to the force being applied to the closing handle; and therefore, greater clamping forces can be more easily generated by a user. The multi-starburst swivel adapter 26 and base unit handle 34 are especially useful when it is desired to mount additional devices near the head support 20.

While the invention has been illustrated by the description of one embodiment and while the embodiment has been described in considerable detail, there is no intention to restrict nor in any way limit the scope of the appended claims to such detail. Additional advantages and modifications will readily appear to those who are skilled in the art.

Therefore, the invention in its broadest aspects is not limited to the specific details shown and described. Consequently, departures may be made from the details described herein without departing from the spirit and scope of the claims which follow.

What is claimed is:

1. A swivel adapter connectable to, and extending outward from, a head support comprising:
   an elongated base having upper and lower ends comprising:
      an outboard first side facing in an outward direction away from the swivel adapter and an inboard side facing in an inward direction, the inboard side including a connector for removably connecting a head support on the inboard side of the base, the connector comprising first engagement teeth for mateably engaging with like engagement teeth of a head support, and a passage therethrough concentric with a longitudinal axis of the connector, and
      a boss extending from the outboard side in the outward direction and comprising a pivot axis axially aligned with the longitudinal axis of the connector and having a pivot surface;
   a center adapter pivotably mounted on the pivot surface of the boss, and further comprising:
      a split bore formed therein and oriented perpendicular to the boss, and
      a device connector facing in the outward direction, the device connector having second engagement teeth for engageaby contacting like engagement teeth of an additional surgical device, so as to removably hold the additional device;
   a clamp comprising;
      a handle pivotally connected to the center adapter on one side of the split bore and pivotal about a handle pivot pin having a handle axis,
      a rocker pivotally connected to the center adapter on an opposite side of the split bore and pivotal about a rocker pivot pin having a rocker axis, the rocker axis and the handle axis being parallel,
      a tubular adjuster comprising a tubular body secured to the rocker at a first end and having an opening at a second end,
      a rod having first and second ends, the second end of the rod telescopically received within the second end of the tubular adjuster and the rod pivotally connected to the handle at the first end thereof, so as to span the split bore; and
      a biasing means disposed between an internal shoulder of the tubular adjuster and the second end of the rod for facilitating movement of the clamp from a clamped orientation to an unclamped orientation wherein the rod is biased towards a retracted position within the tubular adjuster and applies a clamping force between the handle pivot pin and the rocker pivot pin and opposing sides of the split bore when the clamp is in the clamped orientation the handle being operable to clamp the center adapter on the pivot surface of the boss at a desired orientation and to unclamp the center adapter from the pivot surface of the boss, thereby allowing the center adapter to rotate with respect to the boss so as to locate the device connector at a desired rotated position relative to the boss.

2. The swivel adapter of claim 1 wherein the biasing means is includes a plurality of Belville springs.

3. A swivel adapter comprising:
   an elongated base having first and second ends, the first end defining an outboard side facing in an outward direction and an inboard side facing in an inward direction;
   a head support connector located at the inboard side of the first end of the base, the head support connector comprising first engagement teeth for mateably engaging like engagement teeth of a head support, and a passage therethrough concentric with a longitudinal axis of the connector:
   a boss extending outwardly from the outboard side of the base and comprising a pivot axis aligned with the longitudinal axis of the head support connector the boss defining a pivot surface thereabout and a passage therethrough;
   a center adapter with a cylindrically shaped opening sized to receive the boss such that the center adapter is pivotably mounted on the pivot surface, the center adapter having a first device connector facing in the outboard direction, the first device connector adapted having second engagement teeth for engageably contacting like engagement teeth of an additional surgical device, so as to removably hold the additional device;
   a handle operatively connected to the boss, the handle having an elongated shank extending through the cylindrically shaped opening of the center adapter, the passage of the boss and the passage of the head connector, the shank threadably engageable with the head support such that threaded tightening of the shank within the head support secures the first engagement teeth with teeth of the head support at a desired orientation and removably secures the head support to the inboard side of the base;
   clamp operatively connected to the center adapter, the clamp including a clamp operator operable to clamp the center adapter on the pivot surface of the boss at a desired orientation with respect to the base, and to unclamp the center adapter from the pivot surface, thereby allowing the center adapter to rotate with respect to the pivot surface, the pivoting of the center adapter about the boss via the clamp operator being independent of the removable securement of the head support via the handle, with both the clamp operator and the handle being controllable from the outboard side of the base.

4. The swivel adapter of claim 3 wherein the pivot surface is on a cylindrical boss and the center adapter has a split bore mounted over the cylindrical boss.

5. The swivel adapter of claim 4 wherein the clamp comprises:
   a handle pivotally connected to the center adapter on one side of the split bore;
   a rocker pivotally connected to the center adapter on an opposite side of the split bore;
   a rod pivotally connected to the handle at a first end thereof and operatively connected to the rocker at a second end thereof, so as to span the split bore ; and
   biasing means disposed between the first and the second ends of the rod for facilitating movement of the clamp operator from a clamped orientation to an unclamped orientation.

6. The swivel adapter of claim 5 wherein the rocker further comprises means for variably adjusting the biasing means, thereby to vary the force needed to move the clamp operator from the clamped orientation to the unclamped orientation.

7. The swivel adapter of claim 6 wherein the biasing means comprises a plurality of Belville springs.

* * * * *

UNITED STATES PATENT AND TRADEMARK OFFICE
CERTIFICATE OF CORRECTION

PATENT NO. : 7,544,007 B2  Page 1 of 1
APPLICATION NO. : 10/549876
DATED : June 9, 2009
INVENTOR(S) : Kevin R. Easton It is certified that error appears in the above-identified patent and that said Letters Patent is hereby corrected as shown below:

Column 5, line approximately 14, reads ". . .by tightening an releasing. . ." and should read --. . . by tightening and releasing. . .--.

Column 9, line 14, reads ". . .wherein the biasing means is includes. . ." and should read --. . .wherein the biasing means includes. . .--.

Column 9, line 34, reads ". . .adapted having second. . ." and should read --. . .having second. . .--.

Column 10, line 7, reads ". . .clamp operatively connected. . ." and should read --. . .a clamp operatively connected. . .--.

Signed and Sealed this

Thirtieth Day of March, 2010

David J. Kappos
*Director of the United States Patent and Trademark Office*